United States Patent [19]

Wellman

[11] Patent Number: 5,096,503
[45] Date of Patent: Mar. 17, 1992

[54] BODY WASTE BAG WASHER

[76] Inventor: Sidney E. Wellman, 926 W. 29th St., Erie, Pa. 16508

[21] Appl. No.: 656,455

[22] Filed: Feb. 19, 1991

[51] Int. Cl.$^5$ ................................................ B08B 9/00
[52] U.S. Cl. .............................. 134/22.18; 134/167 R; 137/625.48; 137/801; 604/332
[58] Field of Search ............ 137/872, 873, 801, 625.48; 604/332, 334; 134/166 R, 167 R, 22.1, 22.18

[56] References Cited

U.S. PATENT DOCUMENTS

| | | | |
|---|---|---|---|
| 1,687,012 | 10/1928 | Forth . | |
| 2,223,566 | 12/1940 | Koch | 128/283 |
| 2,782,785 | 2/1957 | Arcand | 128/283 |
| 3,736,934 | 6/1973 | Hennessy | 128/283 |
| 3,802,503 | 4/1974 | Sasaki | 137/872 X |
| 4,159,042 | 6/1979 | Getman | 137/625.48 X |
| 4,194,506 | 3/1980 | Voorhies | 128/283 |
| 4,692,159 | 9/1987 | Kuzemchak | 604/277 |
| 4,941,878 | 7/1990 | Petrik | 605/105 |

Primary Examiner—Alan Cohan
Attorney, Agent, or Firm—Charles L. Lovercheck; Wayne L. Lovercheck

[57] ABSTRACT

An apparatus for washing body waste bags that have an opening. The apparatus includes a diverter valve having an internally threaded spout to attach to a faucet. The diverter valve has a plunger and a reduced size nipple adapted to be received in a small opening in a body waste bag. When the faucet is turned on and the plunger is in an diverter open position, the water from the faucet flows normally through the diverter valve for regular use into the bag to wash the bag. When the plunger is in a closed position the water flows through reduced size openings to wash the bag. The diverter valve will remain on the faucet for convenient later use for cleaning body waste bags.

1 Claim, 1 Drawing Sheet

BODY WASTE BAG WASHER

BACKGROUND OF THE INVENTION

This invention relates to surgical bags and more particular to colostomy and urostomy bags.

Users of body waste bags require facilities to periodically wash such bags. No simple, convenient or efficient equipment is available for washing such bags. Heretofore, equipment has been provided to conveniently and efficiently connect urostomy and colostomy bags to a stream of water from water faucets. Examples of efforts to provide such equipment are shown in the following U.S. Pat. Nos. 3,736,934 to Hennessy; 4,194,506 to Voorhies; 4,692,159 to Kuzemchak and 4,941,878 to Petrick. Other prior art is shown in the following U.S. Pat. Nos. 1,687,012 to Forth; 2,223,566 to Koch and 2,782,785 to Arcand. None of these apparatuses have a convenient connector on a faucet that can be left in place for convenient and immediate use and are easily connectable to such bags.

BACKGROUND OF THE INVENTION

The present invention provides a readily available and convenient way to connect a body waste bag, such as a urostomy bag or a colostomy bag, to a water faucet for cleaning the bag. Applicant has discovered that the tube from a colostomy bag or a urostomy bag can be connected directly to the water from an ordinary water faucet through a diverter valve having a small easily available nipple as an outlet, so that without interfering with its use at other times the water from the faucet can be diverted from the faucet into the waste bag to wash the bag. Thus, providing a convenient means of washing the bag.

The diverter valve can be left in place and the faucet used for its intended purpose with little or no interruption. The diverter valve shown in the present invention has a second opening considerably smaller than the main valve opening directing a suitable amount of water for washing the bag and provides a convenient connection for the bag to the water faucet. By using a part of the water, a large amount of water that could otherwise interfere with the washing operation might come from the faucet is eliminated and the undesirable results due to large amounts of water can be avoided, yet sufficient flow of water to efficiently wash the bag. The tubing from the bag will easily slip over the diverter nipple and the diverter valve will provide a convenient connection for water to the bag.

Applicant has discovered that by diverting a part of the water from the water faucet through a small nipple, a neat workmanlike thorough washing procedure can be carried out. Frequent washing of the bag will extend its useful life many fold.

Another object of the invention is to provide a convenient apparatus for washing body waste bags that can be permanently left in place on a water faucet without interfering with the normal use of the faucet.

Another object of the invention to provide a convenient device for washing body waste bags that utilizes a small fraction of the water flow from a water faucet and is simple, economical and efficient to use.

With the above and other objects in view the present invention consists of the combination and arrangement of parts hereinafter more fully described, illustrated in the accompanying drawing and more particularly pointed out in the appended claims its being understood that changes may be made in the form, size, proportions and minor details of construction without departing from the spirit or sacrificing any of the advantages of the invention.

DESCRIPTION OF THE PREFERRED EMBODIMENTS

Figure 1:
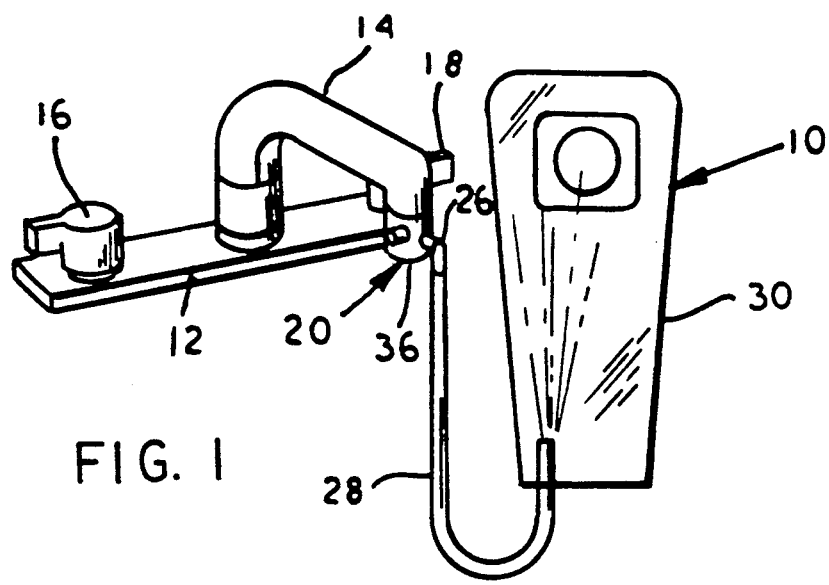
FIG. 1 is an isometric view of the apparatus according to the invention connected to a colostomy or urostomy bag.

Now with more particular reference to the drawings, apparatus 10 consists of faucet 12 and diverter valve 20. Faucet 12 could be any suitable kind of faucet familiar to those skilled in the art that are found in bathrooms, kitchens or other rooms. Faucet 12 has spout 14 which has threaded faucet outlet 19 suitable to be attached to the threaded end 23 of diverter valve 20. Faucet 12 has hot water handle 16 and cold water handle 18 which controls the flow of water to spout 14 in a conventional manner.

Figure 2:
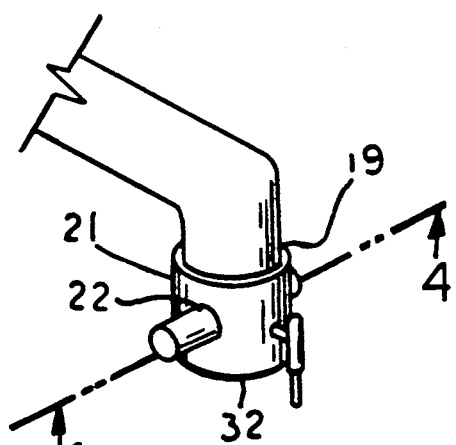
FIG. 2 is a diverter valve connected to a faucet with the diverter valve in a closed position.
Figure 3:
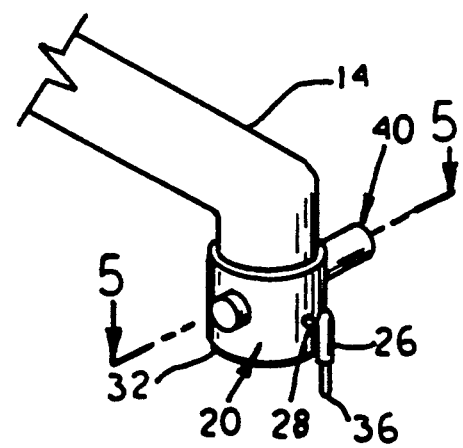
FIG. 3 is a diverter valve connected to a faucet with the diverter valve in an open position.
Figure 4:
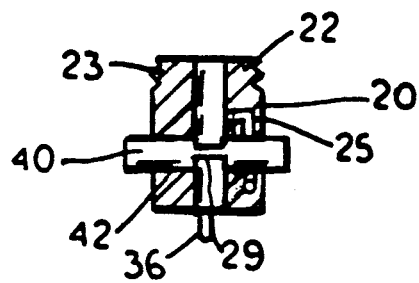
FIG. 4 is a longitudinal cross sectional view taken on line 4—4 of FIG. 2.

Diverter valve 20 has hollow body 21 with flow passage 22 through it with outlet 32 and transverse bore 42 in which plunger 40 is slidably received. Inner diverter channel 25 is formed in a wall of diverter valve 20 and communicates with transverse bore 42 and groove passage 29 in plunger 40 when plunger 40 is in the position shown in FIG. 5, so that water can flow from spout 14 through inner diverter channel 25 and outer diverter channel 24 to outlet tube 28. When the plunger has been pushed to the positions shown in FIGS. 2 and 4, groove 29 is out of alignment with outer diverter channel 24 and inner diverter channel 25 in hollow body 21 and in alignment with flow passages 22 in hollow body 21 and faucet 12.

Figure 5:
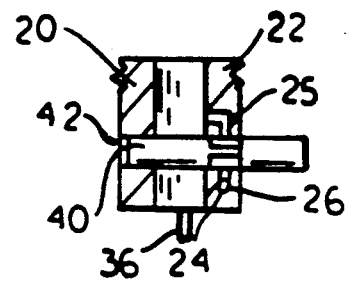
FIG. 5 is a longitudinal cross sectional view of the diverter valve taken on line 5—5 of FIG. 3.

To wash body waste bag 30, the user can connect outlet tube 28 to nipple 26 and move plunger 40 on diverter valve 20 to the position shown in FIG. 5 which connects water from faucet 12 through diverter valve 20 through nipple 26 connected to end member 36 to body waste bag 30 to clean body waste bag 30 when body waste bag 30 has been cleaned. Plunger 40 can then be moved to the positions shown in FIGS. 2 and 4, stopping the flow to the nipple 26. Outlet tube 28 can be removed from nipple 26 and faucet 12 is ready for general use.

Body waste bag 30 may be of any design that has an opening suitable for connecting outlet tube 28 to nipple 26.

The foregoing specification sets forth the invention in its preferred, practical forms but the structure shown is capable of modification within a range of equivalents without departing from the invention which is to be understood is broadly novel as is commensurate with the appended claims.

The embodiments of the invention in which I claim an exclusive property or privilege is claimed are defined as follows:

1. A method of cleaning a body waste bag including providing a faucet, a diverter valve having a grooved plunger, an inlet, an outlet and a nipple;
   connecting said nipple to said body waste bag;
   connecting said diverter valve to said faucet;
   turning on said faucet to connect water to said diverter valve;
   moving said plunger to a first position thereby connecting said water to said nipple;
   holding said body waste bag manually and allowing said water from said faucet to flow into said body waste bag to clean said body waste bag;
   removing said body waste bag from said nipple;
   moving said plunger to a second position thereby cutting off water to said nipple;
   turning off said faucet and,
   emptying soiled water from said body waste bag.

* * * * *